United States Patent
Kuster et al.

(10) Patent No.: US 10,823,947 B2
(45) Date of Patent: Nov. 3, 2020

(54) ILLUMINATION FILTER SYSTEM AND OBSERVATION SYSTEM FOR A MULTISPECTRAL FLUORESCENCE MICROSCOPE, MULTISPECTRAL FLUORESCENCE MICROSCOPE, AND MICROSCOPYING METHOD

(71) Applicant: LEICA INSTRUMENTS (SINGAPORE) PTE. LTD., Singapore (SG)

(72) Inventors: Manfred Kuster, Widnau (CH); George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 355 days.

(21) Appl. No.: 15/424,815

(22) Filed: Feb. 4, 2017

(65) Prior Publication Data
US 2017/0235118 A1   Aug. 17, 2017

(30) Foreign Application Priority Data
Feb. 15, 2016   (EP) .................................. 16155623

(51) Int. Cl.
*G02B 21/16* (2006.01)
*A61B 1/04* (2006.01)
(Continued)

(52) U.S. Cl.
CPC .......... *G02B 21/16* (2013.01); *A61B 1/00186* (2013.01); *A61B 1/043* (2013.01);
(Continued)

(58) Field of Classification Search
CPC ...... G02B 21/16; G02B 21/0012; G02B 5/28; G01N 21/6458; G01N 2201/061;
(Continued)

(56) References Cited

U.S. PATENT DOCUMENTS 4,368,974 A    1/1983  Coote et al.
5,710,663 A *  1/1998  Kawasaki ............ G02B 21/082
                                                        359/368
(Continued)

FOREIGN PATENT DOCUMENTS

CN    103654700 A    3/2014
CN    105136756 A   12/2015
(Continued)

OTHER PUBLICATIONS

De Grand, et al., An Operational Near-Infrared Fluorrescence Imaging System Prototype for Large Animal Surgery, Technology in Cancer Research & Treatment, vol. 2, No. 6, 10 pages Dec. 1, 2003.
(Continued)

*Primary Examiner* — Sanjay Cattungal
(74) *Attorney, Agent, or Firm* — Hodgson Russ LLP (57) ABSTRACT

The present invention relates to an illumination filter system (2) for medical imaging, in particular multispectral fluorescence imaging, as performed e.g. in a microscope (1) or endoscope, such as a surgical microscope, in particular a surgical multispectral fluorescence microscope, comprising a first optical filter (35). The present invention also relates to an observation system (3) for medical imaging, in particular multispectral fluorescence imaging, as performed e.g. in a microscope (1) or endoscope, in particular a multispectral fluorescence microscope, comprising a beam splitter (21) adapted to split a light image (13) into a first light portion (16, 17) along a first light path (18) and a second light portion (20) along a second light path (19). To improve known illumination filter systems and observation systems, so these systems work with one light source only, are capable of capturing simultaneously at least one fluorescence signal and a signal of visible reflected light and allow a homogeneous illumination for obtaining different images from the object illuminated, the first optical filter (36) is
(Continued)

adapted to quench light of at least one fluorescence excitation band within the visible spectrum in the illumination filter system (2) of the present invention, and the first light portion (16, 17) comprises at least one fluorescence emission band (Em.1, Em.2) in the visible spectrum and the second light portion (20) portion comprises a visible reflected light (VISR) in the observation system (3) of the present invention.

11 Claims, 6 Drawing Sheets (51) Int. Cl.
*G02B 5/28* (2006.01)
*A61B 1/045* (2006.01)
*A61B 1/06* (2006.01)
*A61B 1/00* (2006.01)
*A61B 5/00* (2006.01)
*G01N 21/64* (2006.01)
*G02B 21/00* (2006.01)

(52) U.S. Cl.
CPC ............ *A61B 1/045* (2013.01); *A61B 1/0646* (2013.01); *A61B 5/0071* (2013.01); *G01N 21/6458* (2013.01); *G02B 5/28* (2013.01); *G02B 21/0012* (2013.01); *G01N 2021/6419* (2013.01); *G01N 2021/6471* (2013.01); *G01N 2201/061* (2013.01)

(58) Field of Classification Search
CPC .... G01N 2021/6471; G01N 2021/6419; A61B 5/0071; A61B 1/00186; A61B 1/043; A61B 1/0646; A61B 1/045
USPC ................................................ 600/473–480
See application file for complete search history.

(56) References Cited

U.S. PATENT DOCUMENTS

| | | | |
|---|---|---|---|
| 6,198,532 B1 * | 3/2001 | Cabib | A61B 5/14555 250/461.2 |
| 2003/0011910 A1 | 1/2003 | Weiss | |
| 2003/0078477 A1 * | 4/2003 | Kang | A61B 1/042 600/178 |
| 2008/0255426 A1 * | 10/2008 | Iketani | A61B 1/043 600/180 |
| 2012/0268573 A1 * | 10/2012 | Schonborn | A61B 1/051 348/49 |
| 2012/0300294 A1 | 11/2012 | Jess et al. | |
| 2013/0307953 A1 | 11/2013 | Hauger et al. | |
| 2013/0338747 A1 * | 12/2013 | Kondabatni | A61N 1/05 607/116 |
| 2014/0027653 A1 * | 1/2014 | Mori | G02B 5/22 250/458.1 |
| 2014/0330355 A1 * | 11/2014 | Stevenson | A61N 1/08 607/116 |
| 2015/0018690 A1 | 1/2015 | Kang et al. | |
| 2015/0238085 A1 * | 8/2015 | Inoue | A61B 1/00096 600/317 |
| 2015/0305604 A1 * | 10/2015 | Melsky | A61B 5/0084 600/104 |
| 2016/0361120 A1 * | 12/2016 | Brinkmann | A61B 18/26 |
| 2017/0038572 A1 | 2/2017 | Mori et al. | |

FOREIGN PATENT DOCUMENTS

| | | |
|---|---|---|
| CN | 105222891 A | 1/2016 |
| DE | 102011002990 | 7/2012 |
| GB | 2075698 | 11/1981 |
| WO | 2013109966 | 7/2013 |

OTHER PUBLICATIONS

Sato, et al., Development of a new high-resolution intraoperative imaging system (dual-image videoangiography, DIVA) to simultaneously visualize light ande near-infrared fluorescence images of indocyanine green angiography, Acta Neurochirurgica, vol. 157, No. 8, pp. 1295-1301 Jul. 8, 2015.

* cited by examiner

ILLUMINATION FILTER SYSTEM AND OBSERVATION SYSTEM FOR A MULTISPECTRAL FLUORESCENCE MICROSCOPE, MULTISPECTRAL FLUORESCENCE MICROSCOPE, AND MICROSCOPYING METHOD

CROSS REFERENCE TO RELATED APPLICATIONS

This application claims priority of European patent application number 16155623.8 filed Feb. 15, 2016, the entire disclosure of which is incorporated by reference herein.

FIELD OF THE INVENTION

The present invention relates to an illumination filter system for medical imaging, in particular multispectral fluorescence imaging, as performed e.g. in a microscope or an endoscope, such as a surgical microscope, in particular a surgical multispectral fluorescence microscope, comprising a first optical filter. The invention also relates to an observation system for medical imaging, in particular multispectral fluorescence imaging, as performed e. g. in a microscope or endoscope, such as a surgical microscope, in particular a surgical multispectral fluorescence microscope, comprising a beam splitter adapted to split a light image, such as an image received from an illuminated object, into a first light portion along a first light path and a second light portion along a second light path.

Furthermore, the invention relates to a medical imaging apparatus, such as a microscope or endoscope, or a surgical microscope, in particular a surgical multispectral fluorescence microscope, comprising such illumination filter system and/or observation system. The invention also relates to a medical imaging method, such as a microscopying method or endoscopying method for illuminating and observing an object, the method comprising illuminating the object with illumination light, wherein a light image received from the illuminated object is split into a first light portion along a first light path and a second light portion along a second light path.

BACKGROUND OF THE INVENTION

Microscope systems for imaging a color image of reflected visible light and a fluorescence image from an object simultaneously are known from e.g. De Grand and Frangioni, "Operational near-infrared fluorescence imaging system prototype for large animal surgery", Technology in Cancer Research & Treatment, Volume 2, No. 6, December 2003, pp 1-10, or from Sato et al. "Development of a new high-resolution intraoperative imaging system (dual-image videoangiography, DIVA) to simultaneously visualize light and near-infrared fluorescence images of indocyanine green angiography", Acta Neurochirurgica (2015), Volume 157, pp 1295-1301. These systems require two light sources, an illumination filter system for each light source as well as an observation system for capturing the image of visible reflected light as well as fluorescence light emitted from the object. Using two light sources is equipment intensive, costly and requires bulky instrumentation. Further, these systems show inhomogeneities in illumination due to the two light sources used, and only one fluorophore can be used at a time with these systems.

SUMMARY OF THE INVENTION

It is therefore the object of the present invention to improve the known illumination filter systems and observation systems for medical imaging, in particular multispectral fluorescence imaging, as performed e.g. in for a microscope or endoscope, such as a surgical microscope, in particular a surgical multispectral fluorescence microscope, so these systems work with one light source only, are capable of capturing simultaneously at least one fluorescence signal and a signal of reflected visible light and allow a homogeneous illumination for obtaining different images from the object illuminated.

This object is achieved for the illumination filter system as initially mentioned in that the first optical filter is adapted to quench light of at least one fluorescence emission band within the visible spectrum.

For the observation system mentioned in the beginning, this object is solved in that the beam splitter is adapted to split a light image into a first light portion comprising at least one fluorescence emission band in the visible spectrum along the first light path and into a second light portion comprising reflected visible light along the second light path.

For the imaging method initially mentioned, this problem is solved by splitting the light received from the illuminated object into a first light portion comprising at least one fluorescence emission band in the visible spectrum along the first light path and a second light portion comprising reflected visible light along the second light path.

The inventive illumination filter system may simultaneously capture at least one florescence signal and a signal of reflected light with one light source only because the first optical filter merely quenches a fluorescence emission band within the visible spectrum. In the sense of the present application, the visible spectrum is light with a wavelength of 390 to 780 nm. This way, only the wavelength corresponding to the fluorescence signal, namely the fluorescence emission band is removed, while light of other wavelength, e.g. visible light and fluorescence excitation light may pass the first optical filter. This allows to simultaneously capture a fluorescence signal and a visible signal from the object illuminated by the illumination system.

The inventive observation system allows to simultaneously capture visible reflected images of the object as well as at least one fluorescence signal from the object observed because of the specific beam splitter encompassed. This allows for a more time-efficient observation as different fluorescent signals need not be captured one after another. The same applies to the imaging method of the present invention.

The solutions according to the invention can be improved by the following advantageous features, which are independent of one another and can be combined independently. Further, all features described with respect to the inventive apparatus can be used and accordingly applied in the inventive microscopying method.

For example, the inventive illumination filter system may be adapted for multispectral imaging, in particular multispectral fluorescence imaging. The illumination filter system may be adapted for a multispectral fluorescence microscope. Such multispectral fluorescence microscope acquires simultaneously at least two, preferably three or more images, such as for example two or more fluorescence signals, or a visible reflectance image as well as at least two fluorescence signals. The preceding list is not exhaustive and the illumination filter system can be easily adapted to the required multispectral image to be acquired.

According to an embodiment of the illumination filter system, the first optical filter may be adapted to quench light with a wavelength of 500-560 nm and/or light with a wavelength of 620-650 nm. Light with a wavelength of 500-560 nm corresponds to the emission spectrum (or band) of fluorescein. Light with wavelengths of 620-650 nm corresponds to the emission spectrum of the fluorophore 5-amino levolinic acid-induced protoporphyrin IX (S-ALA/ppIX).

At least two fluorescence signals can be captured simultaneously, together with a signal of visible reflected light, if the first optical filter is adapted to quench light of at least two fluorescence emission bands within the visible spectrum. The first optical filter may be adapted to quench light within a wavelength of 500-560 nm and light with a wavelength of 620-650 nm. With such filter, a fluorescein signal as well as a 5-ALA/ppIX signal may be simultaneously captured with an image of visible reflected light using one light source only.

In one embodiment, the illumination filter system may further comprises a second optical filter adapted to attenuate light of a fluorescence excitation band. The second optical filter may be adapted to attenuate light with a wavelength of 390-420 nm and/or light with a wavelength of 750-800 nm. Using a second filter adapted to attenuate light with a wavelength of 390-420 nm, the intensity of light in the excitation band of fluorescene and 5-ALA/ppIX may be reduced. When the second optical filter is adapted to attenuate light with a wavelength of 750-800 nm, the intensity of light in the excitation band of indocyanine green (ICG) may be reduced. The second optical filter may be used to avoid unnecessary damaging of the observed object, which may be important when using the illumination filter system in a surgical microscope for observing tissue that is sensitive to light in the range of fluorescence excitation bands. To avoid damaging the tissue, the second optical filter may be used, together with or instead of the first optical filter, e.g. in case of capturing a visible image only.

In one embodiment, the second optical filter may be configured to be moved from a first operation position, in which the second optical filter is in optical communication with the first optical filter, to a second operation position, in which the second optical filter is out of optical communication with the first optical filter. The first optical filter and the second optical filter, if in its first operation position, are in optical communication, which means that illumination light directed onto and passing through the first optical filter subsequently meets and passes the second optical filter in its first operation position. In other words, the expression "optical communication" means that the respective elements are arranged along the same light path.

Alternative embodiments for directing a light beam through the optical filters of the illumination filter system may be applicable. It is possible to configure each of the first optical filter and the second optical filter to be moveable from the first operation position, in which the optical filter is in optical communication with a light source, to a second operation position in which the optical filter is out of optical communication with the light source, wherein the first optical filter is in its first operation position when the second optical filter is in its second operation position and vice versa. It is also possible to use an illumination filter system, wherein the first optical filter and the second optical filter are arranged out of optical communication with each other and wherein the light source of the microscope is configured to be moved from a first operation position, in which the light source is in optical communication with the first optical filter to a second operation position, in which the light source is in optical communication with the second optical filter.

In another example, the first optical filter may be band-stop filter that may quench all fluorescence emission bands. For example, if three fluorescent signals are to be captured, the first optical filter may be a triple-band-stop filter quenching the corresponding three fluorescence emission bands. It is also possible to use multiple single-band-stop filters arranged in series, i.e. in optical communication one after another.

The second optical filter may be a band-stop filter that may attenuate all fluorescence excitation bands. In the example of acquiring three fluorescence signals simultaneously, the second band-stop filter could be a triple-band-stop filter attenuating light of all three fluorescence excitation bands. Likewise, a system with three single-band-stop filters in series may be used as second band-stop filter.

According to the present application, quenching light means that essentially all light of the respective wavelength is eliminated. Attenuating light in the sense of the present application means that light of the respective wavelength is diminished. Quenching is a specific embodiment of attenuating all light of the respective wavelength.

The expression "out of optical communication with the first band-stop filter" means that the second optical filter, in its second operation position, may be either arranged completely out of the illumination path, or that the second band-stop filter comprises an illumination path area, which transmits essentially light of all wavelengths.

The first optical filter may be a band-stop filter adapted to transmit the fluorescence excitation bands and visible light, except for the quench fluorescence emission bands falling into the spectrum of visible light.

In one exemplary embodiment, the first optical filter may be a notch filter, for example a dual-notch filter in case two fluorescence signals are to be captured simultaneously, or a triple-notch filter in case three fluorescence images are to be captured simultaneously, and so on. Likewise, more than one notch filter element may be arranged in a series as the first optical filter in order to eliminate light of any fluorescence emission band to be captured.

The second optical filter may also be a band-stop filter. It may be adapted to transmit all wavelengths of visible light except the attenuated fluorescence excitation bands in the visible spectrum.

In a further embodiment, the illumination filter system may comprise a third optical filter adapted to transmit light of a fluorescence excitation band only. The third optical filter may transmit light having the wavelength of all fluorescence excitation bands necessary to excite the respective fluorophore in the object to be observed only.

The third optical filter may be a band-pass filter. The third optical filter may be configured to be moved from a first operation position, in which the third optical filter is in optical communication with the first optical filter (and preferably also with the second optical filter in its first operational position), to a second operation position, in which the third optical filter is out of optical communication with the first optical filter.

Attenuating the fluorescence excitation bands by the second optical filter allows adjustment of the intensity of fluorescence excitation and may be used to quench the fluorescence excitation in case the illumination filter system is to be used without a fluorescence mode thus avoiding unnecessary exposure of tissue to excitation light.

The second optical filter may be adapted to adjust the degree of attenuation of the fluorescence excitation bands. Adjusting the degree of attenuation allows an adjustment of the intensity of the excitation light relative to the intensity of white (or visible) light providing a homogenous illumination of the object and improving the quality of the signals/image captured in a microscope using the inventive illumination filter system. The illumination filter system may comprise a control system that is adapted to adjust the degree of attenuation. For example, the second optical filter may comprise a series of filter elements or filter zones having different degrees of attenuation, i.e. attenuating light of the fluorescence excitation band to different degrees. Such a system could, for example comprise three different filters, one completely quenching the light of the fluorescence excitation bands, another one having transmittance of 50-75% of the fluorescence excitation bands and a third filter having transmittance of about 25-50% of the fluorescence excitation bands. The control system may be configured to move the respective filter into optical communication with the first optical filter in order to achieve the intended degree of attenuation. In a further embodiment, the second optical filter may be a variable filter comprising a plurality of attenuation elements or attenuation areas, each having a different transmittance for the fluorescence excitation bands and thus allowing to vary the degree of attenuation.

In a further embodiment, the second optical filter may comprise a spatial band-stop filter pattern, said spatial pattern having coverage of 100% of a first illumination path on the second optical filter and having coverage of less than 100% of a second illumination path on the second optical filter. The band-stop filter pattern may be a band-stop filter coating applied as a spatial pattern on a substrate. "Coverage" is that portion or fraction of an illumination path with filters the light passing through the illumination path. E.g. coverage of 80% means that 80% of the light passing the illumination pass is filtered, while the other 20% of light passes unfiltered. The coverage may be achieved, e.g. by embedding a certain amount of filtering compound in or by coating a certain amount of filtering material on the filter in the respective illumination path.

The third optical filter may comprise a spatial band-pass filter pattern, said spatial pattern having coverage of 100% of the first illumination path on/through the third optical filter and having coverage of less than 100% of the second illumination path on the third optical filter. The band-pass filter pattern may be a band-pass filter coating applied as a spatial pattern on a substrate.

The expression "illumination path" defines a specific area the illumination light path covers on the filter. If the filter is displaced with respect to a light source, the illumination path on the filter likewise changes. In this respect, it is to be noted that different illumination paths on the filter may partially overlap. Thus, a plurality of different illumination paths may be provided on a single filter.

The filter, or substrate in case of a filter with a patterned coating on a substrate, may essentially transmit all illumination light. E. g. the substrate may be a glass substrate. The ratio of coated versus uncoated areas within a specific illumination path determines the percentage of attenuation for said illumination path. The coverage is the ratio of coated area with respect to the total area of an illumination path.

The band-stop filter coating may attenuate always 100% of the respective fluorescence excitation band(s). Thus, the percentage of coating within a specific illumination path determines the degree of attenuation of fluorescence excitation bands in said illumination path.

The band-pass filter coating may always have 100% transmittance for the respective fluorescence excitation bands, while quenching, i.e. eliminating essentially all other wavelengths. Thus, the coverage determines the degree of attenuation of light having a wavelength outside the fluorescence excitation wavelength. Because of this, for example the degree of attenuation of the intensity of white light may be adjusted. The intensity adjustment of the present invention allows to use an illumination system in a microscope having one light source only, such as for example a light source emitting illumination light having a wavelength of e.g. 300-900 nm, preferably of 380-800 nm.

A spatial filter pattern such as for example a filter coating applied in a spatial pattern on a substrate, may likewise allow to adjust the intensity of different fluorescence excitation bands with respect to each other. For example, a substrate may be completely coated with a first coating being a dual band-pass filter coating for a first and a second fluorescence excitation band. The substrate may further be coated in a spatial pattern with a single band-pass filter coating material having 100% transmittance for the second fluorescence excitation band only, said spatial pattern being as described above and below. This way, the relative intensities of the light in the first fluorescence excitation band may be adjusted relative to the intensity of the light in the second fluorescence excitation band.

According to a further embodiment, the spatial pattern may extend over a plurality of illumination paths provided on the substrate and the coverage, i.e. the ratio coated to the total area of the illumination paths, is different in each illumination path. The coverage may either change stepwise or gradually from one illumination path to another.

The plurality of illumination paths may be arranged along an axis of movement on the substrate, along which the respective filter is configured to be moved from its first operation position to its second operation position. For example, the substrate may be a slide, i.e. a glass plate having a substantially rectangular, preferably elongated shape. This slide may be moved along a linear axis of movement along the longitudinal axis of the slide. In another embodiment, the substrate may be disc-shaped, which disc may have a rotational axis of movement. The disc may be rotated about its center in order to shift from the first into the second operation position. Other embodiments are likewise possible. For example, the substrate may have a rectangular shape with different, distinct illumination paths that do not overlap and which may be individually placed in the illumination light path when displacing the substrate accordingly.

In one embodiment, the spatial pattern may comprise a plurality of coating patches, i.e. spots in which the substrates are coated. The center of adjacent patches is preferably spaced essentially equidistant from each other. In order to achieve a different coverage, i.e. a different ratio of coating in a specific illumination path, the area of patches may vary on the substrate. The center of the patch may be the geometrical center, e. g. the center of the circle where the diameters cross each other or the center of a different shape, such as a square, rectangle, rhombus, or parallelogram, where the diagonals intersect. The area of a patch is the surface of the substrate covered by said patch.

In one embodiment, the coating patches may be coating squares. The diagonal length of the squares may vary, preferably along the axis of movement of the substrate. This way, it is possible to obtain a spatial pattern having a gradually dropping coverage along the axis of movement.

For example, in case of the substrate being a slide, a constant number of coating patches/coating squares may be applied in both, the longitudinal as well as the width direction of the slide. In the longitudinal and the width direction, the distance between the adjacent centers of the squares may be the same. In the width direction, all adjacent squares may have the same diagonal length, hence the same area. In the longitudinal direction, the diagonal length and thus the area of the squares may successively increase.

The distance between the centers of patches as well as the length of the patches/squares are preferably significantly smaller than the area of the illumination paths. Significantly smaller means that the distance/length of patches is smaller by an order of 10.

The illumination filter system of the present invention allows to adjust the intensities of different wavelengths of illumination light such as the intensities of fluorescence excitation bands and the white (or visible) light intensity. The present invention allows to adjust these intensities individually, i.e. adjust the intensity of white light with respect to a first fluorescence excitation band or allows to adjust the intensity of the white light and the first fluorescence excitation band with respect to the second fluorescence excitation band. This improves to simultaneously capture the image of visible light reflected from the object as well as the signals of the fluorescence emission bands.

In one embodiment of the observation system, the first light portion comprises at least two fluorescence emission bands. The present invention thus allows to simultaneously capture a color image of visible reflected light from the object as well as two fluorescence bands, at least one is, but also both of which may be out of the visible spectrum, by applying the observation system of the present invention.

The first light portion may comprise light in the wavelength range of 500-560 nm (fluorescein emission band) and/or light in the wavelength range of 620-650 nm (5-ALA/ppIX emission band).

The beam splitter of the observation system may be a polychroic mirror reflecting essentially all of the fluorescence emission bands to be captured and having substantially 100% transmittance of all visible light.

In a further embodiment, the observation system may further comprise, in the first light path, a band-pass filter adapted to transmit light of the fluorescence emission bands only, which allows to focus and improves the fluorescence emission signals detected by e.g. a sensor arranged in optical communication in the first light path with the band-pass filter.

The observation system may further comprise, in the second light path, a band-stop filter adapted to quench light of the fluorescence emission band. The band-stop filter may preferably be adapted to quench light of the fluorescence excitation bands as well. This improves the signal of visible reflected light detected by e.g. a sensor arranged, in optical communication with the band-stop filter, such as for example a color camera like CCD device.

The present invention further relates to a medical imaging apparatus, such as a microscope or endoscope comprising an illumination filter system described above and/or an observation filter system described above.

The present invention further relates to a medical imaging apparatus, wherein the first band-stop filter is arranged in optical communication with a light source. As mentioned above, the medical imaging apparatus may contain a single light source only.

In the following, the invention is described in greater detail in exemplary embodiments with reference to the accompanying figures. The various features in the embodiments may be freely combined as is explained above. If, for a particular application, the advantage which is realized by a particular feature is not needed, this feature can be omitted.

BRIEF DESCRIPTION OF THE DRAWING VIEWS

In the drawings, the same reference numeral is used for elements which correspond to each other with respect to their design and/or their function.

In the drawings.

DETAILED DESCRIPTION OF THE INVENTION

Figure 1:
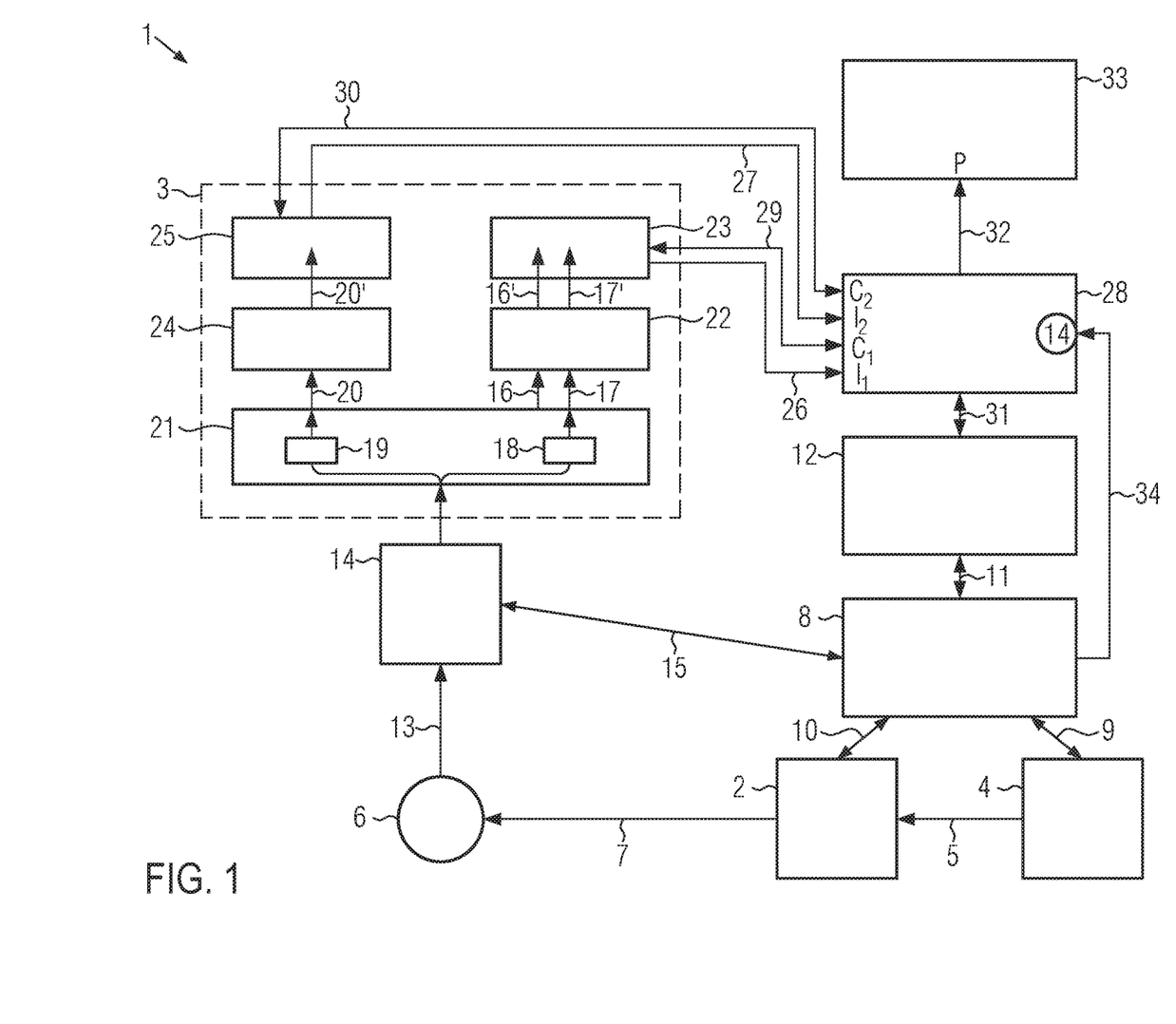
FIG. 1 shows a schematic block diagram of a medical imaging apparatus according to an embodiment of the invention.

First, the design and function of a medical imaging apparatus, such as a microscope 1 or endoscope comprising an exemplary illumination filter system 2 as well as an exemplary observation system 3 is explained with reference to FIG. 1. The microscope 1 comprises a light source 4 that emits an illumination light 5 onto an object 6 to be observed applying a microscopying method according to the present invention. The illumination filter system 2 is in optical communication with the light source 4 as well as the object 6, that is, the illumination system 2 is in the light path of the illumination light 5 from the light source to the object 6.

The illumination filter system 2 filters and spectrally modifies the illumination light 5. It adjusts the intensity of specific portions within the illumination light 5 relative to each other, as will be explained in more detail below with respect to preferred embodiments of the illumination filter system 2 of the present invention. Thus, spectrally modified illumination light 7 exits the illumination filter system 2 and is directed onto the object 6. The spectrally modified illumination light 7 is specifically adapted in order to improve a multi-spectral fluorescence microscopying method. In the shown embodiment, the spectrally modified illumination light 7, provided by the illumination filter system 2, is adapted in order to capture a reflected visible image as well as two fluorescence signals simultaneously, which will also be described in more detail below.

The light source 4 as well as the illumination filter system 2 are both regulated by a controller 8. The controller 8 is connected with the light source 4 via a bi-directional signal line 9, via which the controller 8 may regulate, for example, the intensity of the illumination light 5 or, in case of a light unit having two different light sources, selects the respective light source for emitting the illumination light 5. Via another bi-directional signal line 10, the controller 8 also regulates the illumination filter system 2, e.g. by setting the filters for adjusting the degree of attenuation of certain filters in order to adjust the ratio of light intensities of certain spectral bands included in the spectrally modified illumination light 7. Using bi-directional signal lines 9, 10 allows a loop-control of the settings of the light source 4 and the filter system 2.

The controller 8 itself is coupled via a further bi-directional signal line 11 with a controller interface 12 for inputting settings of the microscope.

A light image 13 is sent from the object 6 to the observation system 3 at defined microscope settings 14. In FIG. 1, the microscope observation settings 14, such as the working distance, magnification, elements used the observation system 3 are represented as a box. The controller 8 may adjust the observation parameters of the microscope via a further signal line 15. The light image 13 sent from object 6 to observation system 3, is split into a first light portion 16, 17 along the first light path 18 and the second light portion 20 along a second light path 19 in a beam splitter 21 of the observation system 3. The first light portion 16, 17 comprises two fluorescence emission bands. The second light portion comprises reflected visible light (VISR), i.e. the visible light reflected from the object. The first light portion 16, 17 passes a band-pass filter 22. The first emission band and the second fluorescence emission band of the first light portion 16', 17' exiting the band-pass filter 22 are captured by the fluorescence sensor 23. The fluorescence sensor 23 may for example be a fluorescence camera, for example, an NIR camera if the fluorescent emission bands are in the near infrared range.

The second light portion 20 passes through the band-stop filter 24. The reflected visible light of the second light portion 20' exiting the band-stop filter 24 is captured by a second sensor 25. The second sensor 25 may be a visible camera such as for example a charge coupled device (CCD).

The first sensor 23, sends, via a signal line 26 a first image read-out $I_1$ comprising information on the captured fluorescence emission bands to a processing unit 28. A second image readout $I_2$ is sent via a signal line 27 from a second sensor 25 to the processing unit 28. The image readout $I_2$ contains the image data of the reflected visible light 20' captured by the sensor 25.

The processing unit 28 is further connected to each of the sensor 23 and the sensor 25 by a bi-directional signal lines 29 and 30, respectively. Via these bi-directional signal lines 29, 30, the processing unit 28 controls the sensors 23 and 25 and reads out the settings of said sensors 23, 25 allowing a loop-control of the sensors 23, 25 by the processing unit 28.

The processing unit 28 itself may receive the settings from a user of the microscope by inputting the corresponding parameters into the controller interface 12 and sending the settings via a signal line 31.

The processing unit 28 may process the image readouts $I_1$ and $I_2$. In a preferred embodiment, a pseudo-image P may be generated by the processing unit 28 and sent from the processing unit 28 via signal line 32 to a display device 33, such as for example, a monitor. Even though it is not shown in FIG. 1, the pseudo-image P may be stored in a documentation system. The pseudo-image P may be a merger of the image readout $I_1$ from the fluorescence (FL) sensor 23 and the VISR image readout $I_2$ from the visible camera 25. It is to be noted that the merged pseudo-image P is not merely an overlay of the image readouts $I_1$ and $I_2$. The pseudo-image P does not obscure any image readout information (which would be the case by overlaying the two image readouts $I_1$ and $I_2$), but rather presents the fluorescence image readout within the VISR image readout $I_2$ in a natural way, resembling the injection of a bright dye. The pseudo-image P may be generated in real time allowing the user of the microscope 1 to capture a combination of the white light image and fluorescence light signals in one merged image.

In order to improve the quality of the pseudo-image P, the image readouts $I_1$ and $I_2$ may be homogenized. The homogenization may correct inhomogeneities in illumination and vignetting of the image optics which would otherwise result in an uneven brightness across the field of view as the periphery of the field of view may be significantly darker at the periphery than in the center. Further, the homogenized image readouts $I_1$ and $I_2$ may be aligned with each other before merging. For example, a spatial correction transformation may be performed to correct alignment errors in the relative position of the two sensors 23 and 25 and digital filters may be applied taking into consideration translation, rotational and magnification mismatches between the sensors 23 and 25. Further, a threshold may be set on an image readout, in particular the image readout $I_1$ received from the fluorescence sensor 23 in order to remove a dark current from the fluorescence sensor 23, thus avoiding a false contribution in measurement of the fluorescence signals.

The controller 8 may provide the processing unit 28, via a signal line 34, with data of the microscope settings 14 that may be inputted by the user via the controller interface 12, such as for example, the working distance, magnification, as well as settings of the illumination filter system 2, the light source 1.

Figure 2A:
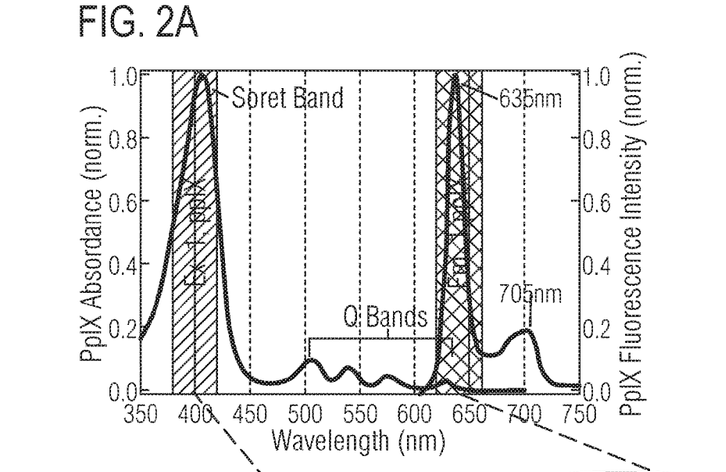
FIG. 2A shows the excitation and emission bands and spectra of 5-ALA/ppIX.
Figure 2B:
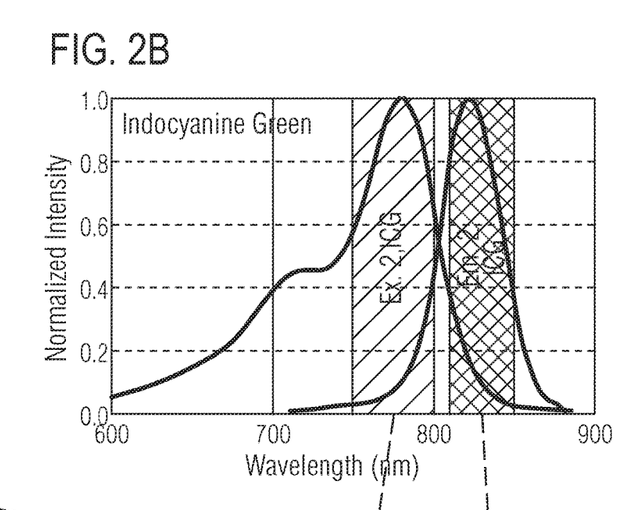
FIG. 2B shows the excitation and emission spectral and bands of Indocyanine Green (ICG)

FIGS. 2A to 2C illustrate the excitation and emission spectra of the fluorophores 5-amino levolinic acid-induced protoporphyrin IX (5-ALA/ppIX) (FIG. 2A) and indocyanine green (ICG) (FIG. 2B). Ex.1, ppIX indicates the excitation band of 5-ALA/ppIX, Em.1, ppIX indicates the fluorescence emission band of protoporphyrin IX, Ex.2, ICG indicates the fluorescent excitation band of ICG, and Em.2, ICG indicates the fluorescence emission band of ICG.

Figure 2C:
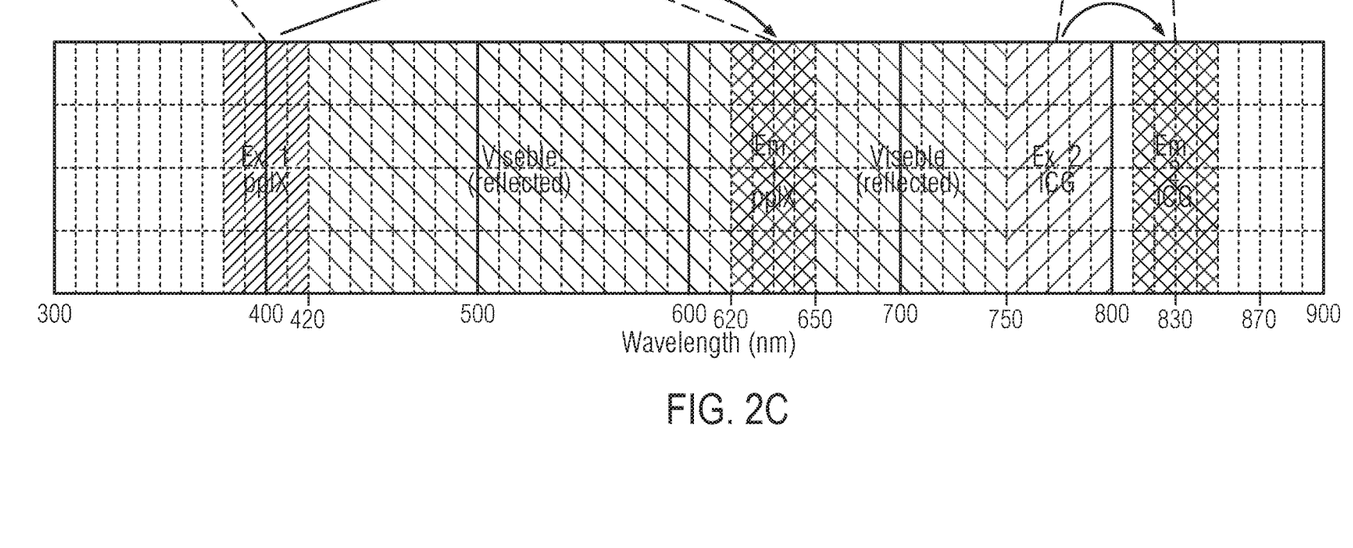
FIG. 2C shows how the spectral portions of the light used in an exemplary embodiment of the present invention is distributed over a spectrum of visible and near infrared (NIR) light.

The graph of FIG. 2C shows the fluorescence excitation and emission bands as well as the visible spectrum, in particular the visible reflected (VISR) light over the wavelengths. As will be explained in more detail below, in the shown exemplary embodiments, the VISR spectrum defined in FIG. 2C is directed onto the second sensor 25, the VISR-sensor. The fluorescence emission bands Em.1, ppIX and Em.2, ICG are directed to the sensor 23, i.e. the fluorescence sensor. Thus, the spectrum of the visible reflected light indicated in FIG. 2C corresponds to the second light portion 20' in FIG. 1. The two fluorescence emission spectra Em.1, ppIX and Em.2, ICG indicated in FIG. 2C correspond to the first light portions 16' and 17', respectively.

In order to clearly distinguish the spectral bands, in particular, exclude the fluorescence excitation band of photoporphyrin IX and avoid an overlapping of the fluorescence excitation bands with the visible spectrum, in particular the visible reflected light, the illumination filter system 2 and the observation system 3 of the present invention are used, as will be explained in the following.

First, the design and function of an exemplary illumination filter system 2 according to a first embodiment is explained with reference to FIGS. 3A and 3B. FIG. 3B shows an exemplary embodiment of an illumination filter system 2 in optical communication with a light source 4. The illumination filter system 2 is arranged in the light path of the illumination light 5. The illumination filter system 2 comprises a first optical filter 35. The first optical filter 35 may be a band-stop filter. The first optical filter 35 is adapted to quench light of the fluorescence emission bands within the visible spectrum. In the shown embodiment, the fluorescence emission bands Em.1 and Em.2 for ppIX and ICG are quenched, respectively. The first optical filter 35 is always in optical communication with the light source 4, thus, the fluorescence emission bands to be detected by sensors 23 are always eliminated from the illumination light 5 by the illumination filter system 2.

The illumination filter system 2 of the shown embodiments furthermore comprises a second optical filter 36. The second optical filter 36, which is optional, may be a band-stop filter. The second optical filter 36 is configured to be moved from a first operation position 37, indicated in dashed lines in FIG. 3B. In the first operation position 37, the second optical filter 36 is in optical communication with the first optical filter 35, that is, the illumination light 5 passes both the first optical filter 35 and the second optical filter 36 when the latter is in its first operation position 37.

The second optical filter 36 is configured to be moved from the first operation position 37 to a second operation position 38, in which the second optical filter 36 is out of optical communication with the first optical filter 35. In a second operation position 38, the second optical filter 36 is not arranged in the light path of the illumination light 5, so the illumination light 5 passes only the first optical filter 35 and not the second optical filter 36 if the latter is in its second operation position 38.

The arrow indicates the transition 39 of the second optical filter 36 from its first operation position 37 to its second operation position 38. This transition 39 may be performed, e.g. by displacing the filter 36 into and out of optical communication with the first optical filter 35.

Figure 3A:
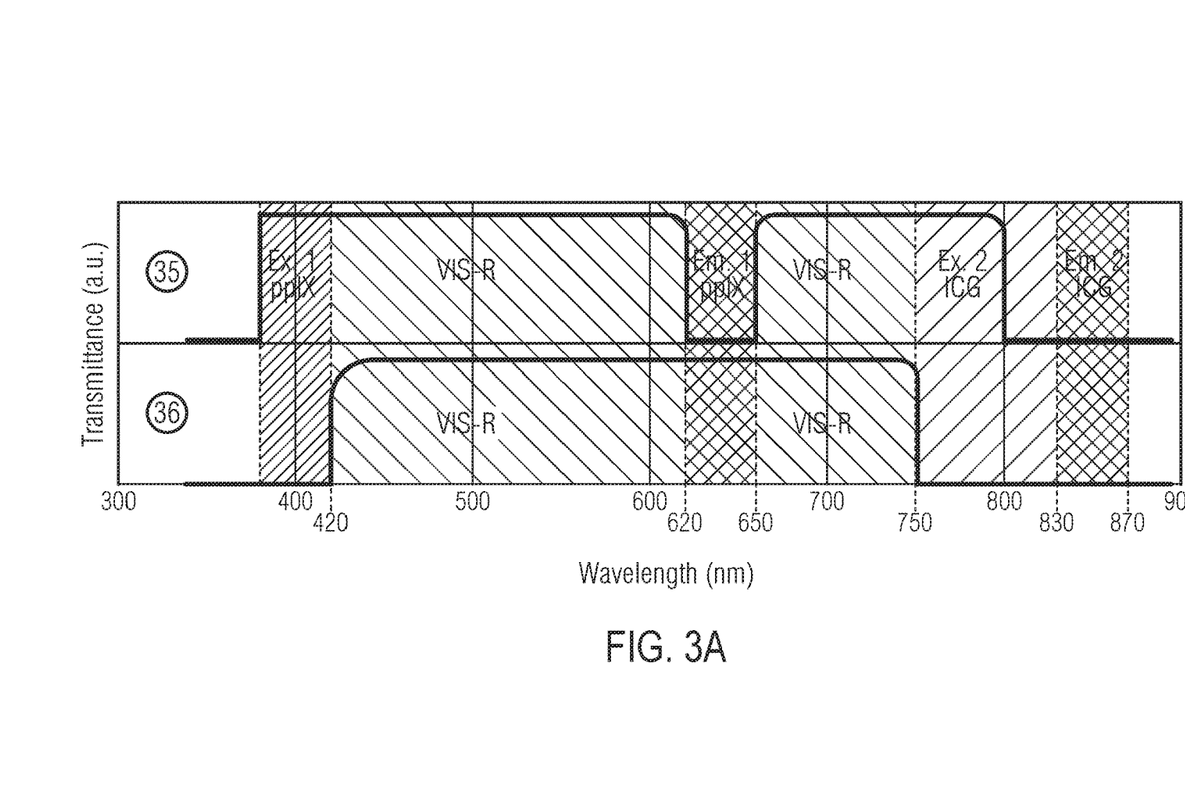
FIG. 3A shows the spectral characteristics (transmittance) of the filters used in an illumination filter system according to a first embodiment.
Figure 3B:
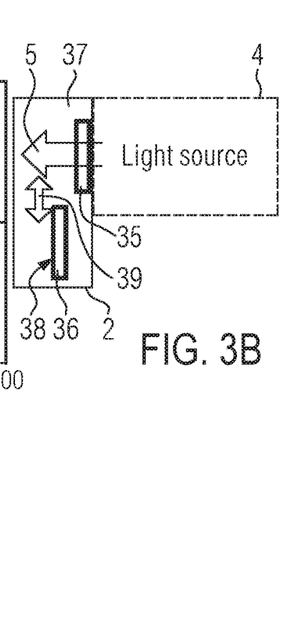
FIG. 3B shows an illumination system of a first embodiment comprising the filters having the spectral characteristics of FIG. 3A.

As can be seen in FIG. 3A, the first optical filter 35 is a band-stop filter adapted to transmit light of the fluorescence excitation bands Ex.1 of ppIX and Ex. 2, ICG as well as the whole spectrum of visible light and a portion of NIR light adjacent to the visible light, except for the quenched fluorescence emission band Em.1 of ppIX.

In one embodiment, the first optical filter 35 may be a dual-notch filter quenching the excitation bands of Em.1 ppIX and Em.2 ICG.

The second optical filter 36 is adapted to transmit the visible reflected light, except for the fluorescence excitation bands Ex.1 and Ex.2 attenuated by said second optical filter 36.

This way, the fluorescence excitation bands may be switched on and off.

The illumination filter system 2 of the present invention allows to adjust the intensity of fluorescence excitation relative to white light and/or the intensity of difference fluorescence excitation bands. Such relative intensity adjustment is useful when for example the maximum excitation power is needed, while maximum white light illumination is too bright for the use of the eyepiece of a microscope.

The illumination filter system 2 of the present invention may also be used to adjust the intensity ratio of the excitation light and the white (or visible) light, for example using an illumination filter system 2 according to a second embodiment. The design and function of the illumination filter system 2 of the second embodiment is explained with reference to FIGS. 3A and 3B in the following.

The design and function of another embodiment of an exemplary illumination filter system 2 will be explained with reference to FIGS. 4 and 5. The embodiment of the illumination filter system 2 shown in FIGS. 4 and 5 comprises the first optical filter 35, which may be a dual-notch filter to eliminate any light at the fluorescence emission bands Em.1, ppIX and Em.2, ICG. The illumination filter system 2 of the embodiment shown in FIGS. 4 and 5 furthermore comprises a second optical filter 36 adapted to attenuate light of the fluorescence excitation bands Ex.1, ppIX and Ex.2, ICG. The second optical filter 36 is configured to be moved from a first operation position 37, in which it is in optical communication with the first optical filter 35, to a second operation position 38. Transition 39 between the first operation position 37 and the second operation position 38 is achieved by moving the second optical filter 36 along an axis of movement 40.

The second optical filter 36 may comprise a rectangular substrate in the shown embodiment a glass slide, 41 and the axis of movement 40 corresponds to the longitudinal direction L of the substrate 41.

A band-stop filter coating 42 is applied in a spatial pattern 43 of the substrate 41, which pattern 43 will be described in more detail below.

Figure 4A:
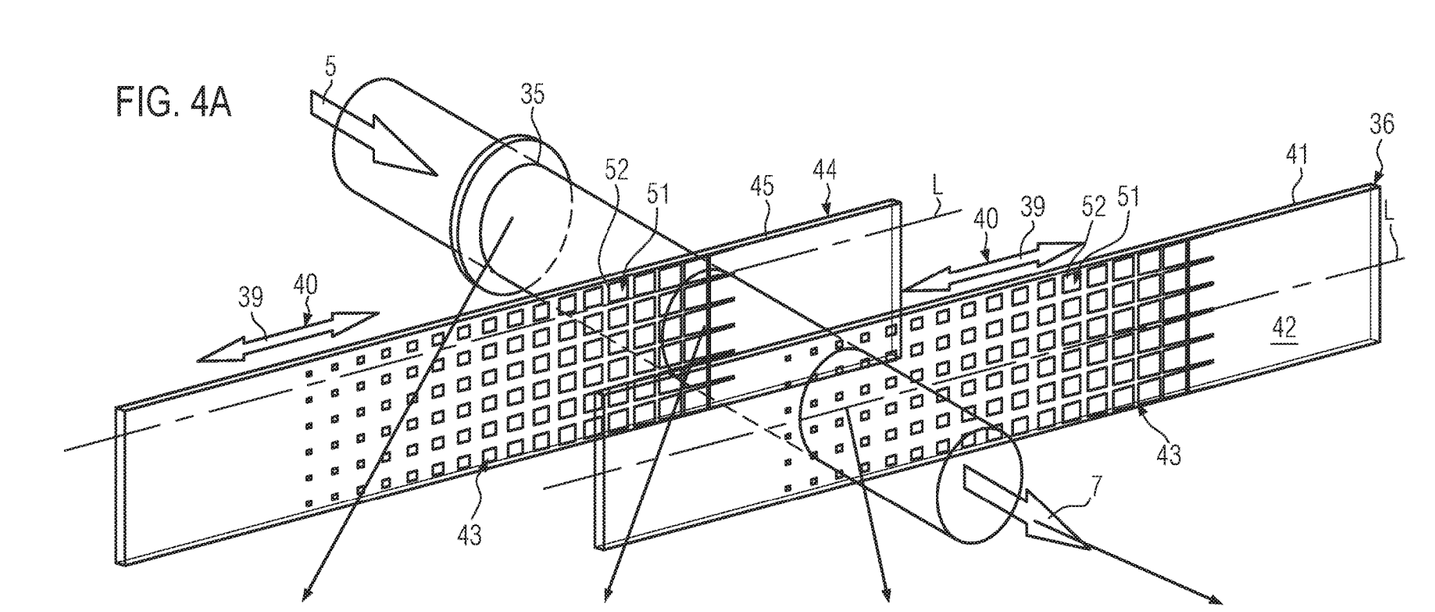
FIG. 4A shows an illumination filter system according to a second embodiment.
Figure 4B:
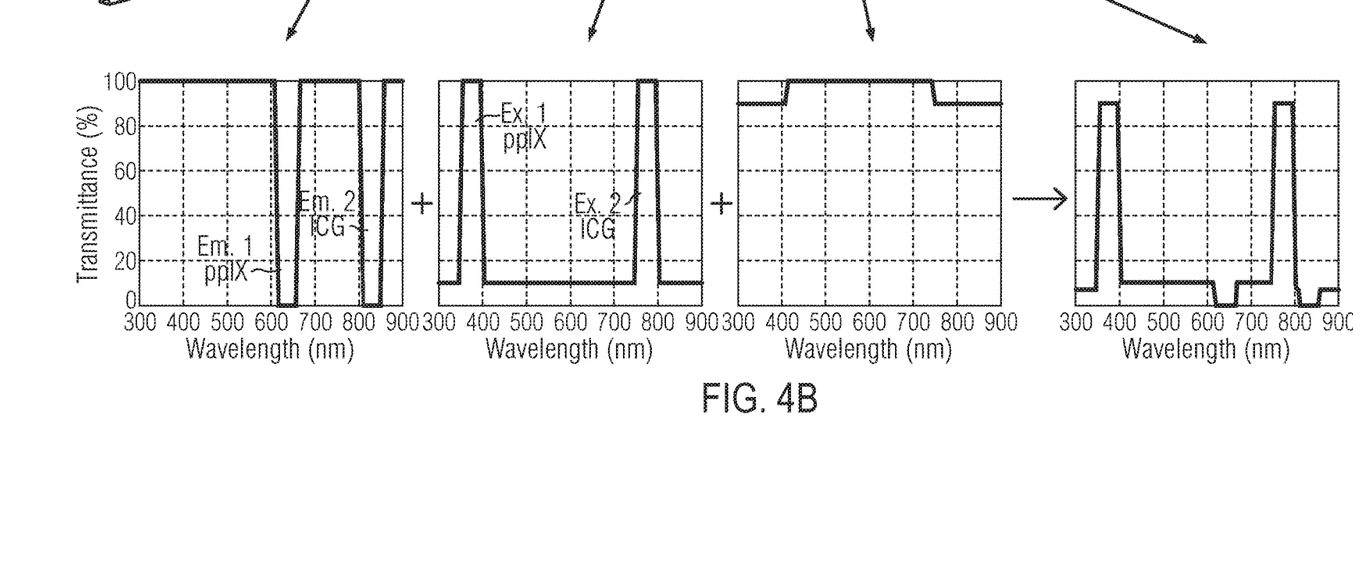
FIG. 4B shows the spectral characteristics of the individual filters encompassed by the illumination filter system as shown in FIG. 4A as well as the spectra characteristics of the whole illumination filter system.

The illumination filter system 2 of the embodiment shown in FIGS. 4 and 5 furthermore comprises a third optical filter 44 adapted to transmit light of the fluorescence excitation bands Ex.1, ppIX and Ex.2, ICG only. The third optical filter 44 may be a band-pass filter 44. Like the second optical filter 36, the third optical filter 44 is configured to be moved from a first operation position 37, in which the third optical filter 44 is in optical communication with the first optical filter 35, to a second operation position 38 in which the third optical filter 44 is out of optical communication with the first optical filter 35.

The third optical filter 44 is likewise comprised in a substrate 45, similar to the substrate 41, which is also composed of a clean glass slide having a rectangular shape, and which can be moved along its longitudinal axis L, which is identical to the axis of movement 40, during transition 39 from the first operation position 37 into the second operation position 38.

The substrate 45 of the third optical filter 44 comprises a band-pass filter coating 46 which is applied in a spatial pattern 43 similar to the spatial pattern 43 of the second optical filter 36 on the substrate 41.

The spatial pattern 43 allows gradual attenuation of the intensity of fluorescence excitation bands Ex.1, ppIX and Ex.2, ICG from 100% to 0% by means of the second optical filter 36 as well as the intensity of the white light from 0 to 100% transmittance by means of the third optical filter 44.

Filters 36 and 44 are variable filters allowing adjustment of transmittance of the fluorescence excitation bands and the white light intensity, respectively, depending on their position in the path of illumination light 5 along the longitudinal direction L/the axis of movement 40. This is achieved by the spatial pattern 43 of coating 42, 46 which is identical in the shown in embodiment for both, the second optical filter 36 and the third optical filter 44.

Figure 5A:
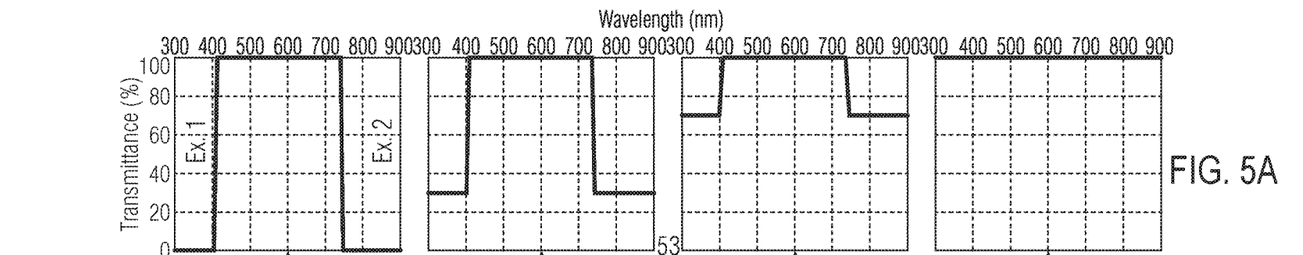
FIG. 5A shows the spectral characteristics of the optical filter of FIG. 5B in the respective illumination path.
Figure 5B:
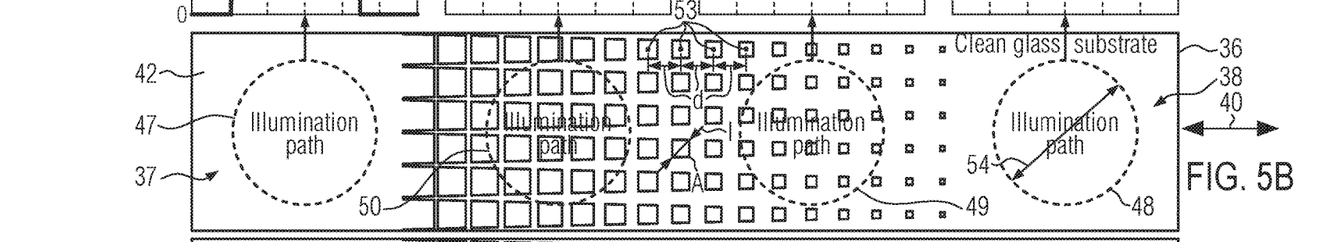
FIG. 5B shows a first variable optical filter having a spatial pattern coating.
Figure 5C:
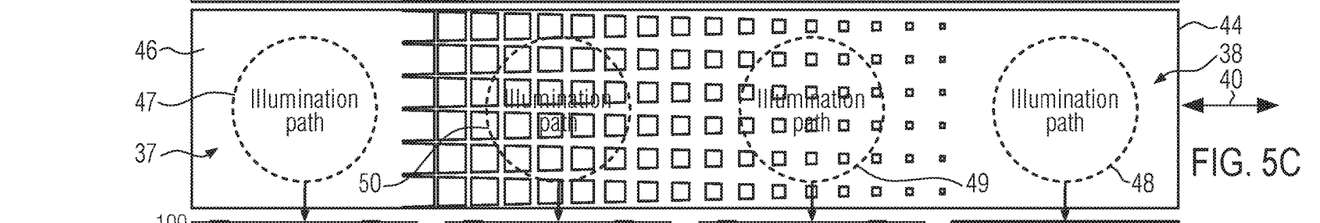
FIG. 5C shows a second variable optical filter having a spatial pattern coating.
Figure 5D:
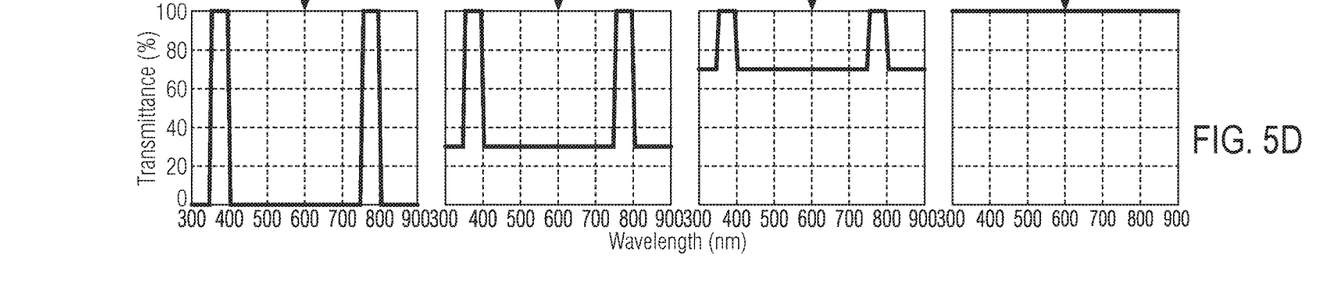
FIG. 5D shows the spectral characteristics of the optical filter of FIG. 5C in the respective illumination path.

The spatial pattern 43 has coverage of 100% of a first illumination path 47. Coverage means the ratio of coated areas with respect to the total area of an illumination path which corresponds to the area of light passing through the respective filters 44, 36 of the illumination filter system 2.

The spatial pattern 43 has coverage of less than 100% of a second illumination path 48 on the substrate 41, 45. In the shown embodiment, the coating coverage is 0% in the exemplary second illumination path 48 meaning that no coating 46 at all is applied to the substrate 41, 45 on the position corresponding to the second illumination path 48, which is thus identical to the second operation position 38, in which the filter is out of optical communication. In between the first illumination path 47, which is on one end of substrate 41, 45 and the second illumination path 48, which is on the opposite end along the longitudinal direction L of the substrate 41, 45, a plurality of illumination paths are provided from which as an example, two further illumination paths 49 and 50 are shown in FIGS. 5B and 5C.

The plurality of illumination paths 48, 49, 50, 47 are arranged along the axis of movement 40 on the substrate 41, 45. The spatial pattern 43 comprises a plurality of coating patches 51. In the shown embodiment, the coating patches 51 are coating squares 52. The center 53 of adjacent patches 51/squares 52 are spaced apart equidistantly, i.e. at the same distance d from one another. However, the area A of the patches 51 varies along the axis of movement 40. In the shown example, the length 1 of the patches 51, corresponds to the diagonal length 1 of the coating squares 52 that varies along the axis of movement 40. In detail, i.e. the diagonal of the coating squares 52 increases gradually from an area adjacent to the second illumination path 48 having no coating in direction along the axis of movement 40 to the first illumination path 47 having complete, i.e. 100% coating. The spatial pattern 43 starts from 100% spatial coverage in the first illumination path 47 shown on the left in FIG. 5, and the coverage drops gradually along the axis of movement 40 until it is completely absent in the second illumination path 48 on the opposite side, the right side shown in FIG. 5.

The coverage, i.e. the ratio of coated versus total area of an illumination path determines the percentage of transmittance of the fluorescence excitation bands in case of a second band-stop filter 36 as well as the transmittance and thus intensity of the white light having a wavelength of about 400-750 nm in the shown embodiment by the band-pass filter 44. This can be seen for the four exemplary illumination path 47 to 50 in FIGS. 5A and 5D.

The intensities of the fluorescence excitation bands as well as the white light potion in the spectrally-modified illumination light 7 can thus be individually adjusted. The combination of all three filters results in a spectrum of the spectrally-modified illumination light 7 with the desired ratio between white light and excitation intensities as it is shown for one example in FIG. 4B. FIG. 4B shows, from left to right, the quenching of the fluorescence emission bands by the dual-notch filter 35, the attenuation of the white light portion by the band-pass filter 44, the attenuation of the fluorescence excitation light by the second band-stop filter 36. All three of these filters are in optic communication and result in the spectrally-modified illumination light 7 shown on the right side of FIG. 4B.

In order to obtain a nearly gradual changing coverage of the coating 42, 46, the distance d between the centers 53 of the coating patches 51/coating squares 52 should be significantly shorter than the diameter 54 of an illumination path. This way, filtering becomes more homogeneous. Significantly shorter in this respect means a magnitude of at least 10.

Figure 6A:
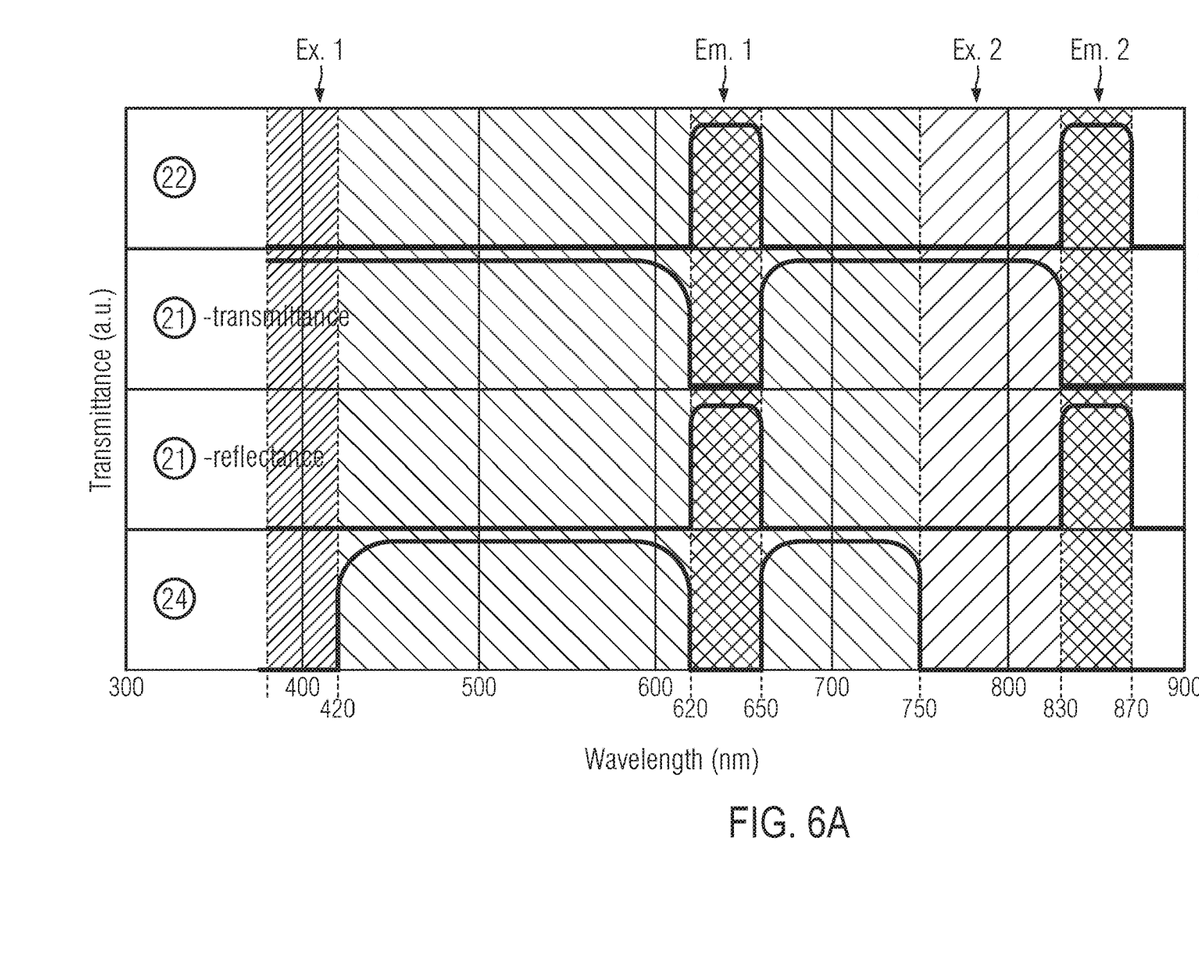
FIG. 6A shows the spectral characteristics (transmittance and reflectance) of filters and the beam splitter of an observation system according to an embodiment of the invention.
Figure 6B:
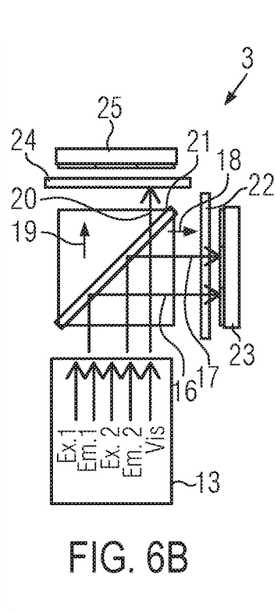
FIG. 6B shows an observation system according to an embodiment comprising filters and a beam splitter having the spectra characteristics shown in FIG. 6A.

Finally, an exemplary embodiment of an observation system 3 is explained with reference to FIG. 6. FIG. 6B shows a schematic design of the observation system 3 and FIG. 6A shows the spectral characteristic (transmittance and reflection) of the components of the observation system 3.

The observation system 3 comprises a beam splitter 21 adapted to split the light image 13 of the illuminated object 6 into a first light portion 16, 17 along a first light path 18 and into a second light portion 20 along a second light path 19. The first light portion 16, 17 comprises the fluorescence emission bands Em.1 of ppIX and Em.2 of ICG. The second portion 20 comprises reflected visible light. In the shown embodiment, the beam splitter 21 is a polychroic mirror 55 that reflects light having a wavelength in the fluorescence emission bands Em.1 and Em.2 and transmits all light of the visible spectrum, except for the fluorescence emission band Em.1 falling into the white light spectrum. The observation system 3 furthermore comprises the two filters 22 and 24 as well as the two senses 23 and 25 already explained with respect to FIG. 1 above.

Further, filter 22, through which the first light portion 16, 17 passes before reaching the sensor 23, may be a band-pass filter adapted to transmit light of fluorescence emission bands Em.1 and Em.2 only. The filter 24, through which the second light portion 20 passes before reaching a sensor 25 may be a band-stop filter adapted to quench light of fluorescence emission bands Em.1, Em.2 as well as the fluorescence excitation bands Ex.1, Ex.2.

| REFERENCE NUMERALS | |
| --- | --- |
| 1 | Microscope/Medical imaging apparatus |
| 2 | Illumination Filter System |
| 3 | Observation System |
| 4 | Light Source |
| 5 | Illumination Light |
| 6 | Object |
| 7 | Spectrally Modified Illumination Light |
| 8 | Controller |
| 9 | Signal Line |
| 10 | Signal Line |
| 11 | Signal Line |
| 12 | Controller Interface |
| 13 | Light Image |
| 14 | Microscope Settings |
| 15 | Signal Line |
| 16, 16' | $1^{st}$ Light Portion |
| 17, 17' | $1^{st}$ Light Portion |
| 18 | $1^{st}$ Light Path |
| 19 | $2^{nd}$ Light Path |
| 20 | $2^{nd}$ Light Portion/VISR |
| 21 | Beam Splitter |
| 22 | Band-Pass Filter |
| 23 | $1^{st}$ Sensor/FL-Sensor |
| 24 | Band-Stop Filter |
| 25 | $2^{nd}$ Sensor/VISR-Sensor |
| 26 | Signal Line |
| 27 | Signal Line |
| 28 | Processing Unit |
| 29 | Signal Line |
| 30 | Signal Line |

-continued

REFERENCE NUMERALS

| | |
|---|---|
| 31 | Signal Line |
| 32 | Signal Line |
| 33 | Display Device |
| 34 | Signal Line |
| 35 | 1$^{st}$ Optical (Band-stop) Filter |
| 36 | 2$^{nd}$ Optical (Band-stop) Filter |
| 37 | 1$^{st}$ Operation Position |
| 38 | 2$^{nd}$ Operation Position |
| 39 | Transition |
| 40 | Axis of Movement |
| 41 | Substrate |
| 42 | Band-Stop Filter Coating |
| 43 | Spatial Pattern |
| 44 | 3$^{rd}$ optical (Band-pass) filter |
| 45 | Substrate |
| 46 | Band-Pass Filter Coating |
| 47 | 1$^{st}$ Illumination Path |
| 48 | 2$^{nd}$ Illumination Path |
| 49 | 3$^{rd}$ Illumination Path |
| 50 | 4$^{th}$ Illumination Path |
| 51 | Coating Patch |
| 52 | Coating Square |
| 53 | Center of Coating Patch/Square |
| 54 | Diameter of Illumination Path |
| 55 | Polychroic Mirror |
| A | Area of Coating Patch/Square |
| d | Distance Between Adjacent Centers |
| Ex. 1 | Excitation Band of ppIX |
| Em. 1 | Emission Band of ppIX |
| Ex. 2 | Excitation Band of ICG |
| Em. 2 | Emission Band of ICG |
| $I_1$ | Image Readout (FL) |
| $I_2$ | Image Readout (VISR) |
| L | Longitudinal Direction |
| I | Length of Patch/Diagonal of Square |
| P | Pseudo-image |
| VISR | Visible Reflected Light |

What is claimed is:

1. A medical imaging apparatus comprising:
a light source (4);
an observation system (3) including a beam splitter (21) adapted to split a light image (13) into a first light portion (16, 17) along a first light path (18) and a second light portion (20) along a second light path (19), wherein the first light portion (16, 17) comprises at least one fluorescence emission band (Em.1, Em.2) in the visible spectrum and wherein the second light portion (20) comprises visible reflected light; and
an illumination filter system (2) including a first optical filter (35) adapted to quench light of at least one fluorescence emission band (Em.1, Em.2) within the visible spectrum, wherein the first optical filter is a band-stop filter adapted to transmit all wavelengths of visible light, except for the quenched light of the at least one fluorescence emission band within the visible spectrum;
wherein the first optical filter (35) is arranged in optical communication with the light source (4) and/or the observation system (3).

2. The medical imaging apparatus of claim 1, wherein the first optical filter (35) is adapted to quench light with a wavelength of 500-560 nm and/or light with a wavelength of 620-650 nm.

3. The medical imaging apparatus of claim 1, further comprising a second optical filter (36) adapted to attenuate light of at least one fluorescence excitation band (Ex.1, Ex.2) by reducing but not quenching the light of at least one fluorescence excitation band (Ex.1, Ex.2).

4. The medical imaging apparatus of claim 3, wherein the second optical filter (36) is adapted to attenuate light with a wavelength of 390-420 nm and/or light with a wavelength of 750-800 nm.

5. The medical imaging apparatus of claim 3, wherein the second optical filter (36) is configured to be moved from a first operation position (37), in which the second optical filter (36) is in optical communication with the first optical filter (35), to a second operation position (38), in which the second optical filter (36) is out of optical communication with the first optical filter (35).

6. The medical imaging apparatus of claim 3, wherein the second optical filter (36) is a band-stop filter adapted to transmit all wavelengths of visible light, except the attenuated fluorescence excitation bands (Ex.1, Ex.2).

7. The medical imaging apparatus of claim 3, wherein the second optical filter (36) comprises a spatial band-stop filter pattern (43), said spatial pattern (43) having coverage of 100% of a first illumination path (47) on the second optical filter (36) and having coverage of less than 100% of a second illumination path (48, 49, 50) on the second optical filter (36).

8. The medical imaging apparatus of claim 7, wherein the spatial band-stop filter pattern (43) extends over a plurality of illumination paths (47-50) provided on the second optical filter (36) and the coverage is different in each illumination path (47-50).

9. The medical imaging apparatus of claim 1, wherein the medical imaging apparatus is an endoscope.

10. The medical imaging apparatus of claim 1, wherein the medical imaging apparatus is a microscope.

11. The medical imaging apparatus of claim 10, wherein the medical imaging apparatus is a surgical multispectral fluorescence microscope.

* * * * *